United States Patent [19]

Hoyng et al.

[11] Patent Number: 5,079,253
[45] Date of Patent: Jan. 7, 1992

[54] COMPOSITION FOR THE TOPICAL TREATMENT OF GLAUCOMA OR OCULAR HYPERTENSION

[75] Inventors: Philip Hoyng, Ke Heemstede, Netherlands; Johan W. Stjernschantz, Uppsala, Sweden

[73] Assignee: Pharmacia AB, Uppsala, Sweden

[21] Appl. No.: 278,533

[22] PCT Filed: Mar. 15, 1988

[86] PCT No.: PCT/SE88/00129
§ 371 Date: Nov. 22, 1988
§ 102(e) Date: Nov. 22, 1988

[87] PCT Pub. No.: WO88/07380
PCT Pub. Date: Oct. 6, 1988

[30] Foreign Application Priority Data

Mar. 25, 1987 [SE] Sweden .................... 8701258

[51] Int. Cl.$^5$ ............... A61K 31/52; A61K 31/415; A61K 31/40; A61K 31/135
[52] U.S. Cl. .................... 514/264; 514/392; 514/400; 514/424; 514/653; 514/913
[58] Field of Search ............... 514/263, 913, 653, 264, 514/392, 400, 424

[56] References Cited

U.S. PATENT DOCUMENTS

| | | | |
|---|---|---|---|
| 4,107,306 | 8/1978 | Voorhees | 514/233 |
| 4,164,570 | 8/1979 | Clough et al. | 514/973 |
| 4,425,346 | 1/1984 | Horlington | 514/913 |

FOREIGN PATENT DOCUMENTS 0047339 3/1982 European Pat. Off. .
2390164 12/1978 France .
622703 4/1981 Switzerland .

OTHER PUBLICATIONS

Geutsche Ophtalmologische Gesellschaft in Heidelberg. Bericht Uber die Zudsmmrnkunft, vol. 71, issued 1972 (Munchen) E. Genee, "Wirkung vasoaktiver Pharmaca auf das Glaucomauge", pp. 354–357.
Albrecht von Graefes Archiv fur klinische und experimentelle Ophtalmoloigie vol. 195, issued 1975 (Berlin), E. Genee and T. Geissendorfer, "Blutdruckandernde Medikamente und Augeninnendruck im Tierversuch" pp. 187–194.
Chem. Abst. 83: 157866y(1975), Genee et al.

Primary Examiner—Frederick E. Waddell
Assistant Examiner—Zohren A. Fay
Attorney, Agent, or Firm—Fred Philpitt

[57] ABSTRACT

A method for the topical treatment of glaucoma or ocular hypertension which comprises contacting the surface of the eye with a composition consisting essentially of an effective intraocular pressure reducing amount of a mixture of (a) an adrenergic agonist selected from the group consisting of epinephrine, dipivalylepinephrine, norepinephrine, phenylephrine, clonidine, isoproterenol, salbutamol, metaproterenol and terbutaline, and (b) a phosphodiesterase inhibitor selected from the group consisting of isobutylmethylxanthine, theophyllamine, Rolipram and RO-2017624, in an ophthalmically compatible carrier.

7 Claims, 20 Drawing Sheets

COMPOSITION FOR THE TOPICAL TREATMENT OF GLAUCOMA OR OCULAR HYPERTENSION

The invention provides a composition for topical treatment of glaucoma or ocular hypertension comprising an effective intraocular pressure reducing amount of a mixture of an adrenergic agonist and a phosphodiesterase inhibitor in an opthalmically compatible carrier. Especially ophthalmic compositions comprising a mixture of epinephrine or dipivaloyepinephrine and isobutylmethylxanthine (IBMX) are at present preferred for use in treating glaucoma or ocular hypertension.

Glaucoma is an eye disorder characterized by increased intraocular pressure, cupping of the optic disc, and visual field loss. Although the pathophysiological mechanism of open angle glaucoma is still unknown there is substantial evidence to suggest that increased intraocular pressure is detrimental to the eye, and that the increased intraocular pressure in glaucoma is the most important factor causing degenerative changes in the retina. In one particular form of glaucoma, low tension glaucoma, the actual situation may simply be that the eye is unusually sensitive to pressure and therefore damage may occur at intraocular pressure levels otherwise regarded as physiologically normal. On the other hand, some individuals may exhibit an abnormally high intraocular pressure substantially without any manifest defects in the visual field or optic disc. Such individuals are referred to as ocular hypertensives. If untreated, glaucoma almost invariably leads to blindness. The course of the disease typically is slow with progressive loss of vision. The basical principle of glaucoma treatment is to lower the intraocular pressure, either by drugs, laser treatment or surgery. The modality of treatment with drugs comprises typically instillation of pilocarpine, epinephrine, or topical beta-blocker treatment, e.g. with timolol, as well as systemically administered inhibitors of carbonic anhydrase, e.g. acetazolamide. Cholinesterase inhibitors such as physostigmine and echothiopate may also be employed and have an effect similar to that of pilocarpine.

Although with many of these drugs the positive effects obtained are at least appreciable, concomitant adverse side-effects are often encountered which tend to diminish the usefulness of the drugs and may negatively affect patient compliance. Improvements in these respects are desirable, as well as improvements in drug efficacy.

The intraocular pressure (IOP) can be defined as according to formula (1):

$$IOP = P_e + F \times R \qquad (1)$$

where $P_e$ is the episcleral venous pressure, generally regarded as being around 9 mmHg, F the flow of aqueous humor and R the resistance to outflow of aqueous humor through the trabecular meshwork and adjacent tissue into Schlemm's canal. Drugs that decrease either F or R thus also decrease intraocular pressure. Aqueous humor is produced continuously in the ciliary processes behind the iris, but it is not known whether there is a neural or hormonal regulation of this process.

Adrenergic agonists can be divided into two main groups: alpha adrenergic and beta adrenergic agonists. Each of these groups can further be subdivided into alpha 1 and 2 and beta 1 and 2 respectively. Generally, the alpha receptors of the vascular smooth muscle in the eye are of the alpha 1 or 2 type whereas the presynaptic receptors on the adrenergic nerves are of the alpha 2 type. The receptors of the ciliary epithelium are predominantly of the beta 2 type. The beta-adrenergic receptors in the outflow channels of the aqueous humor are probably also of the beta 2 type predominantly. The presence of alpha receptors in the outflow channels seems to be species dependent.

Norepinephrine is predominantly an alpha-adrenergic agonist, but it does have some beta-adrenergic activity in addition. Epinephrine is predominantly a beta-adrenergic agonist with some alpha-adrenergic activity. Dipivaloyl-epinephrine is an esterified prodrug of epinephrine with the same spectrum of activity as epinephrine. 3-isobutyl-1-methylxanthine (IBMX) is an inhibitor of intracellular phosphodiesterase.

Pharmaceutical preparations containing a combination of adrenergic agonists and phosphodiesterase inhibitors are known per se (see Swiss paten 622703 and French patent 2390164), but not for ophthalmological use.

It is well known that beta-adrenergic impulses in several tissues are mediated intracellularly by a second messenger, cyclic 3'5' adenosine monophosphate (cAMP). cAMP is produced from ATP by a membrane bound enzyme, adenylate cyclase. cAMP is believed further to activate steps in a chain of processes leading to protein phosphorylation and final biologic activity. Generally, it is though that the cAMP step is a process of short duration because cAMP is rapidly and efficiently degraded intracellularly by phosphodiesterases which are present in abundance. The above mentioned cAMP mediated beta-adrenergic system is present also in the ciliary epithelium and the outflow system of the eye. However, particularly since the cAMP-mediated message is thought to be of short duration physiologically, it was not predictable that an increase of intracellular cAMP content would enhance the final biological response, such as a decrease in the intraocular pressure. Furthermore, it would be reasonable to assume that such a mechanism at any rate should not at all apply to alpha-adrenergic agonists since the impulse in that system is not thought to be mediated through an activation of adenylate cyclase and cAMP in the target cells.

Adrenergic agonists such as for instance epinephrine, dipivalylepinephrine or isoproterenol have been used in pharmaceutical preparations (see for instance DE 2330338, EP 47339 and EP 69075).

Alpha-adrenergic agonists such as norepinephrine are likely to decrease the intraocular pressure mainly by causing vasoconstriction in the ciliary processes thereby interfering with secretion of aqueous humor. Beta-adrenergic agonists are likely to have an effect on the outflow of aqueous humor and to thereby decrease the intraocular pressure. It is also possible that beta-adrenergic agonists have some direct inhibiting effect on aqueous humor production. Several review articles on the adrenergic nervous system in the eye can be found in the literature, e.g. Pharmacology of the Eye, Springer Verlag Berlin, Heidelberg New York, Tokyo Ed. Sears, 1984.

The action of various phosphodiesterase inhibitors in an experimental environment has been studied, and reported in for instance Molecular Pharmacology, vol. 23(2), (1983). Neither the relaxation of smooth muscle tissue reported there, nor the vasodilator effect discussed in Br. J. Pharmacology, 70(2), (1980), p. 219-27, could be said to teach towards the use of such inhibitors in ophthalmological preparations even in the light of the fact that in much earlier other contexts vasodilator substances have been suggested for lowering intra-ocular pressure (Deutsche Ophthalmologische Gesellschaft. Bericht über die Zusammenkunft, vol. 71, (1972), p. 354–7.

In U.S. Pat. No. 4,425,346 certain alkyl-substituted xanthines have been used as solubilizing compounds in ophthalmological compositions containing tetrazabicyclic compounds.

The experiments set forth herein, however, demonstrate that a combination of an alpha- or beta-adrenergic agonist with isobutylmethylxanthine (IBMX), a classical and relatively pure phosphodiesterase inhibitor markedly potentiates the intraocular pressure lowering effect of the adrenergic agonist in an unexpected way. Thus, such a combination of an adrenergic agonist and a phosphodiesterase inhibitor may be clinically useful in the treatment of glaucoma by giving a stronger intraocular pressure lowering effect. It should be noted also that the combination offers the advantage of decreasing the required concentration of the adrenergic agonist. This may be important because, not infrequently, adrenergic agonists used in ophthalmology have involved both local and systemic side effects. A further point to be noted is that IBMX per se appears to be only mildly irritating in the eye if any side-reaction at all can be noticed.

The invention provides a composition for topical treatment of glaucoma or ocular hypertension, comprising an effective intraocular pressure reducing amount of a mixture of an adrenergic agonist and a phosphodiesterase inhibitor in an ophthalmically compatible carrier.

Adrenergic agonists useful in this invention include all ophthalmologically acceptable alpha- and beta-adrenergic agonists such as for instance norepinephrine, phenylephrine, clonidine, epinephrine, isoproterenol, salbutamol, meta-proterenol and terbutaline.

Phosphodiesterase inhibitors (or derivatives having basically the same mechanism of action) which are useful in context of the present invention include theophyllamine, Rolipram ®, Ro-201724 and particularly isobutylmethylxanthine (IBMX).

"Rolipram" is a trademark for 4-(3-cyclopentyloxy-4-methoxyphenyl)-2-pyrrolidone and "RO-201724" is a trademark for 4-(3-butoxy-4-methoxybenzyl)-2-imidazolidinone.

The ophthalmically compatible carrier which may be used in this invention comprises e.g. an aqueous solution, such as saline solution, oil solution or ointment containing ophthalmically compatible preservatives, surfactants and agents such as polymers to increase the viscosity. Also drug inserts either soluble or insoluble may be used.

Although several adrenergic agonists may be employed in the present invention the preferred amount to be present in the mixture is from about 1 microgram to about 1,000 micrograms, specifically from about 10 micrograms to about 100 micrograms per application.

The currently preferred effective amount of phosphodiesterase inhibitor to be present in the mixture is from about 1 microgram to about 1,000 micrograms, specifically from about 10 micrograms to about 100 micrograms.

In a preferred embodiment the adrenergic agonist present in the composition is an alpha- or beta-adrenergic agonist, and the phosphodiesterase inhibitor is any compound inhibiting the phosphodiesterase enzyme.

The currently preferred adrenergic agonists are epinephrine or dipivalylepinephrine, and the phosphodiesterase inhibitor is isobutylmethylxanthine (IBMX) or a derivative of IBMX.

This invention also provides a method for treating glaucoma or ocular hypertension. The method comprises contacting the surface of the eye with a composition comprising an effective intraocular pressure reducing amount of a mixture of an adrenergic agonist and a phosphodiesterase inhibitor in an ophthalmically compatible carrier, all compounds as specified above, so as to reduce the intraocular pressure and maintain it on a reduced level.

Various regimens may be employed for treating glaucoma or ocular hypertension. In the preferred embodiment the treatment comprises contacting periodically, at least daily, the ocular surface i.e. the cornea and the conjunctiva with an effective amount of a mixture of the adrenergic agonist and the phosphodiesterase inhibitor to reduce intraocular pressure.

Also disclosed is a method for treating glaucoma or ocular hypertension by separately contacting the surface of the eye with an intraocular pressure reducing amount of the adrenergic agonist and the phosphodiesterase inhibitor in an ophthalmically compatible carrier, so as to reduce the intraocular pressure and maintain it on a reduced level.

In a series of experiments compositions according to the invention were administered to an animal eye and the intraocular pressure in the experimental eye was compared to the pressure in a control eye.

The results from these and comparative tests are presented in FIGS. 1 to 20.

Figure 1:
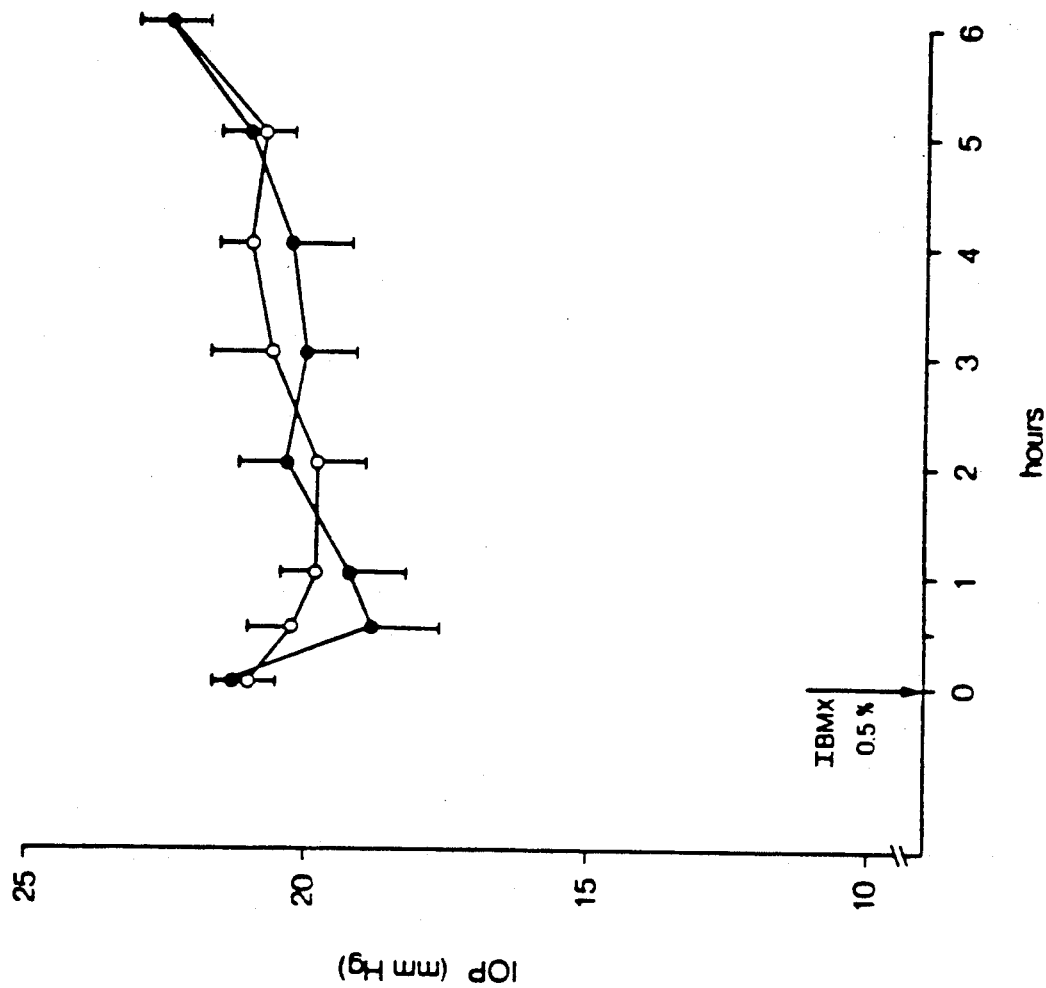
FIG. 1. Effect of 0.5% IBMX on the intraocular pressure in rabbits. There is no statistically significant effect on the intraocular pressure. Dots represent experimental eye, empty circles the control eye.
Figure 2:
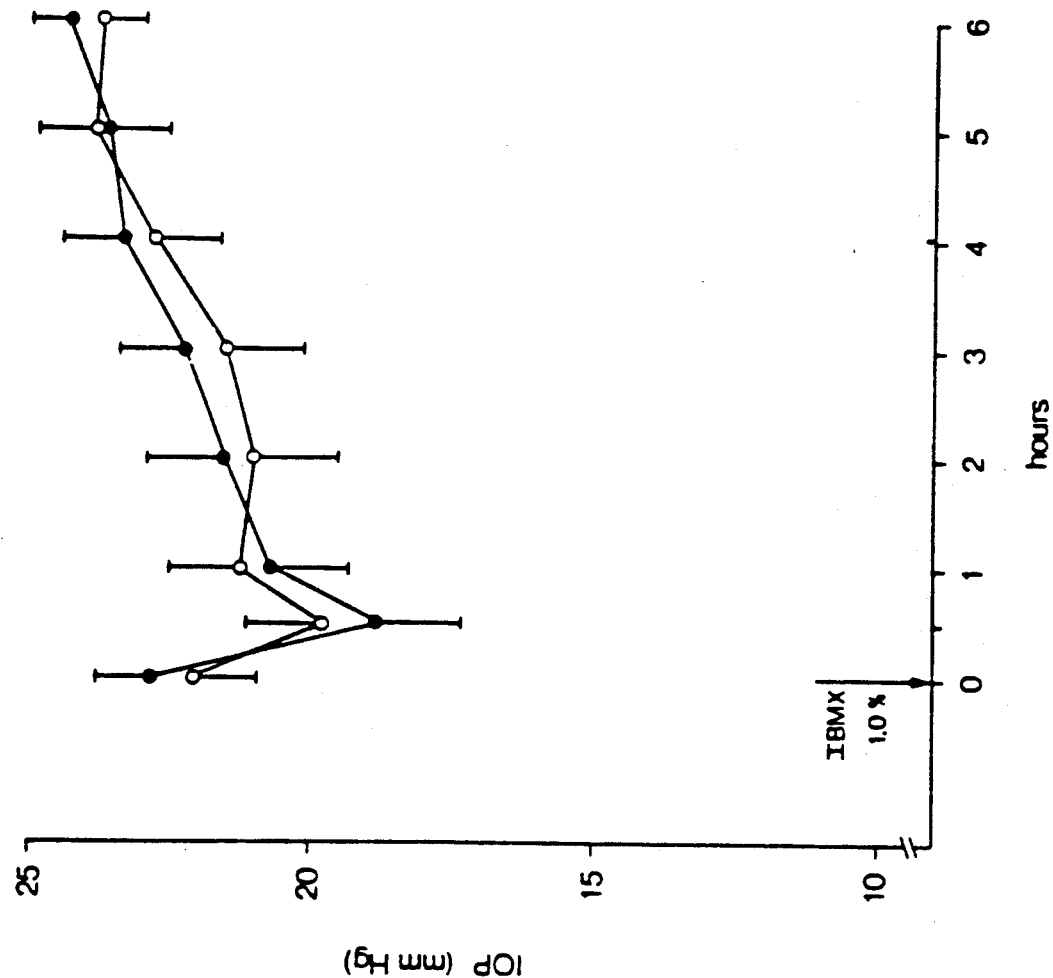
FIG. 2. Effect of 1.0% IBMX on intraocular pressure in rabbits. There is a tendency towards a reduction in pressure, but no statistically significant effect. Dots represent experimental eye and circle the control eye.
Figure 3:
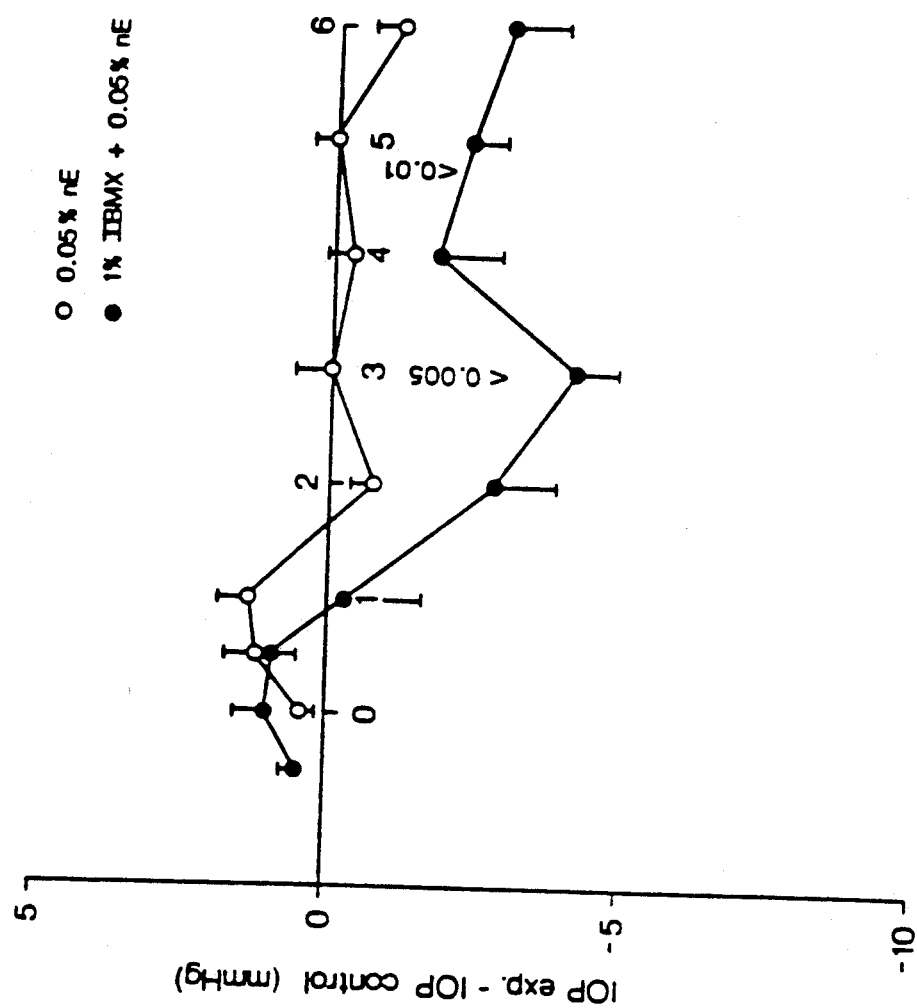
FIG. 3. Difference in intraocular pressure between experimental eyes and control eyes in rabbits treated with 0.05% norepinephrine only (empty circles), and in rabbits treated with a mixture of 1% IBMX and 0.05% norepinephrine. Statistical significances between the experimental and control eyes are indicated between the curves and refer to P-values.
Figure 4:
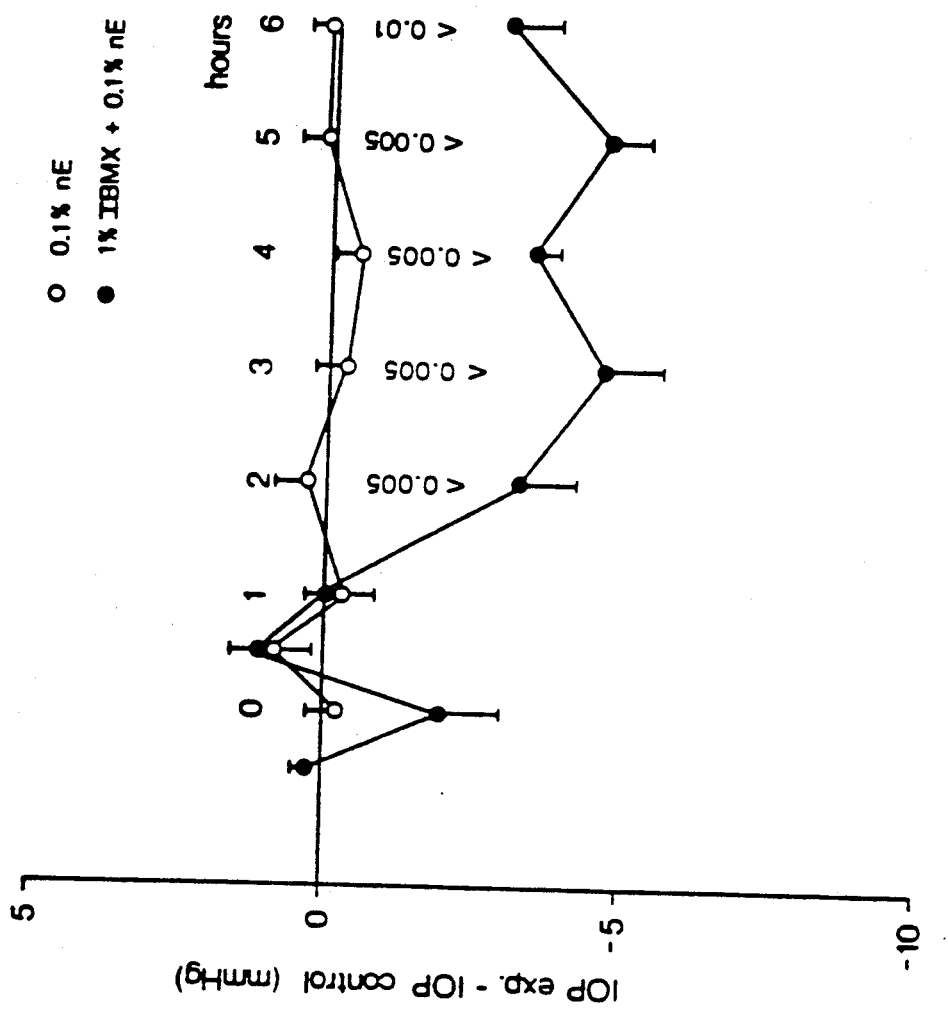
FIG. 4. Difference in intraocular pressure between experimental eyes and control eyes in rabbits treated with 0.1% norepinephrine only (empty circles), and in rabbits treated with 1% IBMX and 0.1% norepinephrine (dots). Statistical significances indicated as in previous figure.
Figure 5:
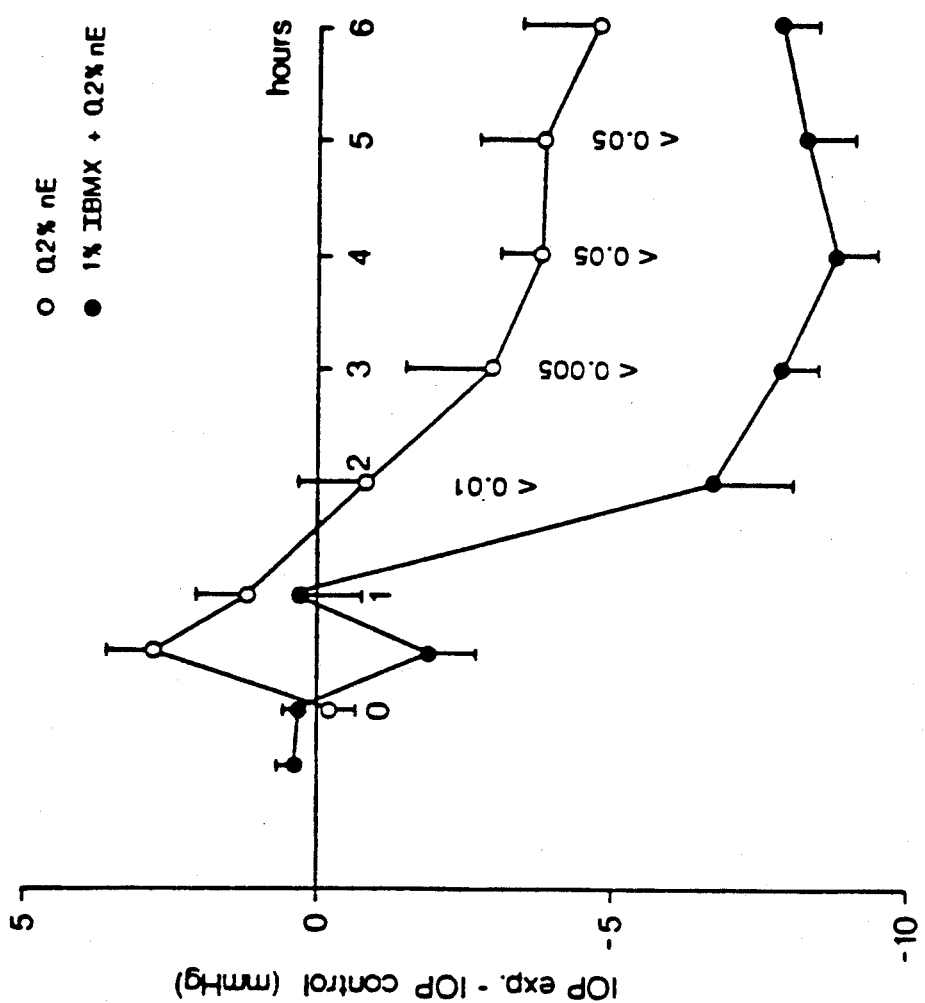
FIG. 5. Difference in intraocular pressure between experimental eyes and control eyes in rabbits treated with 0.2% norepinephrine only (empty circles), and in rabbits treated with 1% IBMX and 0.2% norepinephrine (dots). Statistical significances indicated as in previous figures.
Figure 6:
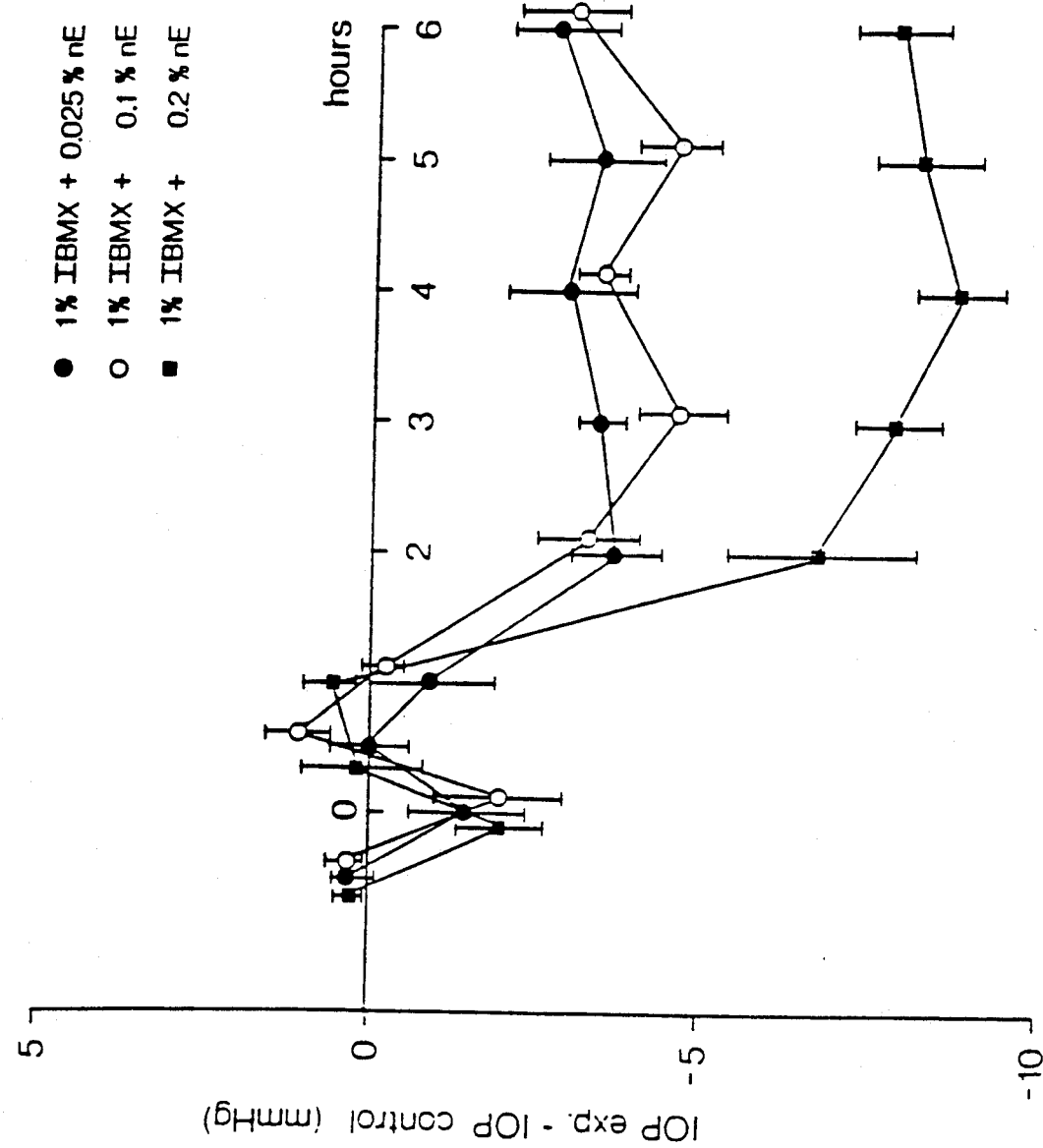
FIG. 6. Difference in intraocular pressure between experimental eyes and control eyes in rabbits treated with 1% IBMX and various concentrations of norepinephrine.

Isobutylmethylxanthine, i.e. phosphodiesterase inhibitors per se have no significant intraocular pressure reducing effect (FIGS. 1-2). However, it is shown (FIGS. 3-6) that in rabbits a combination of (i) 1% isobutylmethylxanthine and (ii) norepinephrine in concentrations ranging from 0.025% to 0.2% causes a significant potentation of the intraocular pressure reducing effect as compared to the administration of norepinephrine alone, in those same concentrations.

Figure 7:
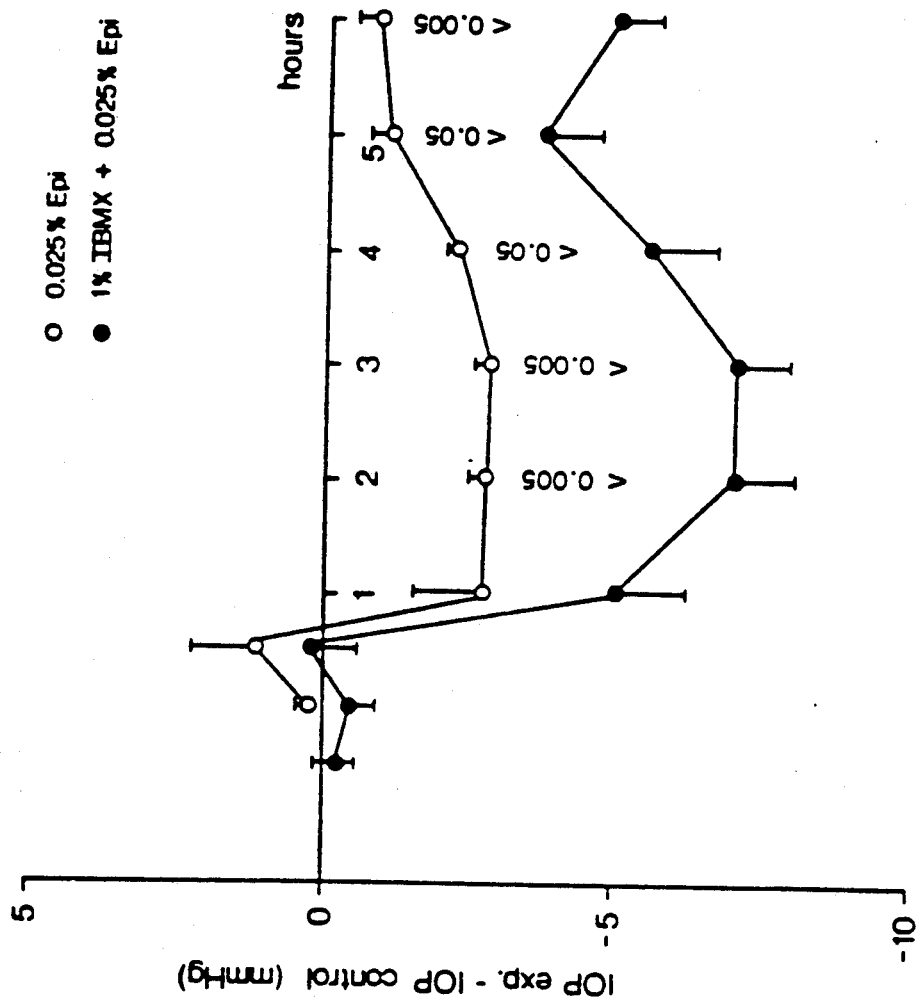
FIG. 7. Difference in intraocular pressure between experimental eyes and control eyes in rabbits treated with 0.025% epinephrine only (empty circles), and in rabbits treated with 1% IBMX and 0.025% epinephrine (dots). Statistical significances indicated as in previous figures.
Figure 8:
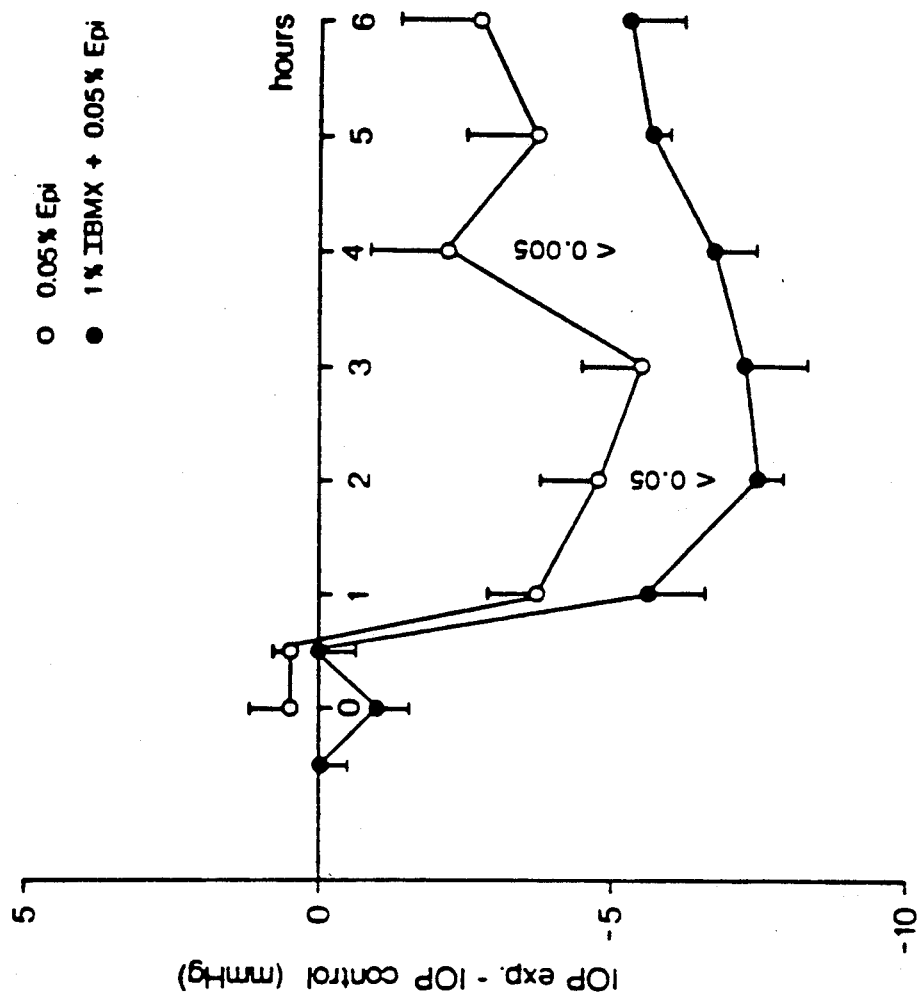
FIG. 8. Difference in intraocular pressure between experimental eyes and control eyes in rabbits treated with 0.05% epinephrine only (empty circles), and in rabbits treated with 1% IBMX and 0.05% epinephrine (dots). Statistical significances indicated as in previous figures.
Figure 9:
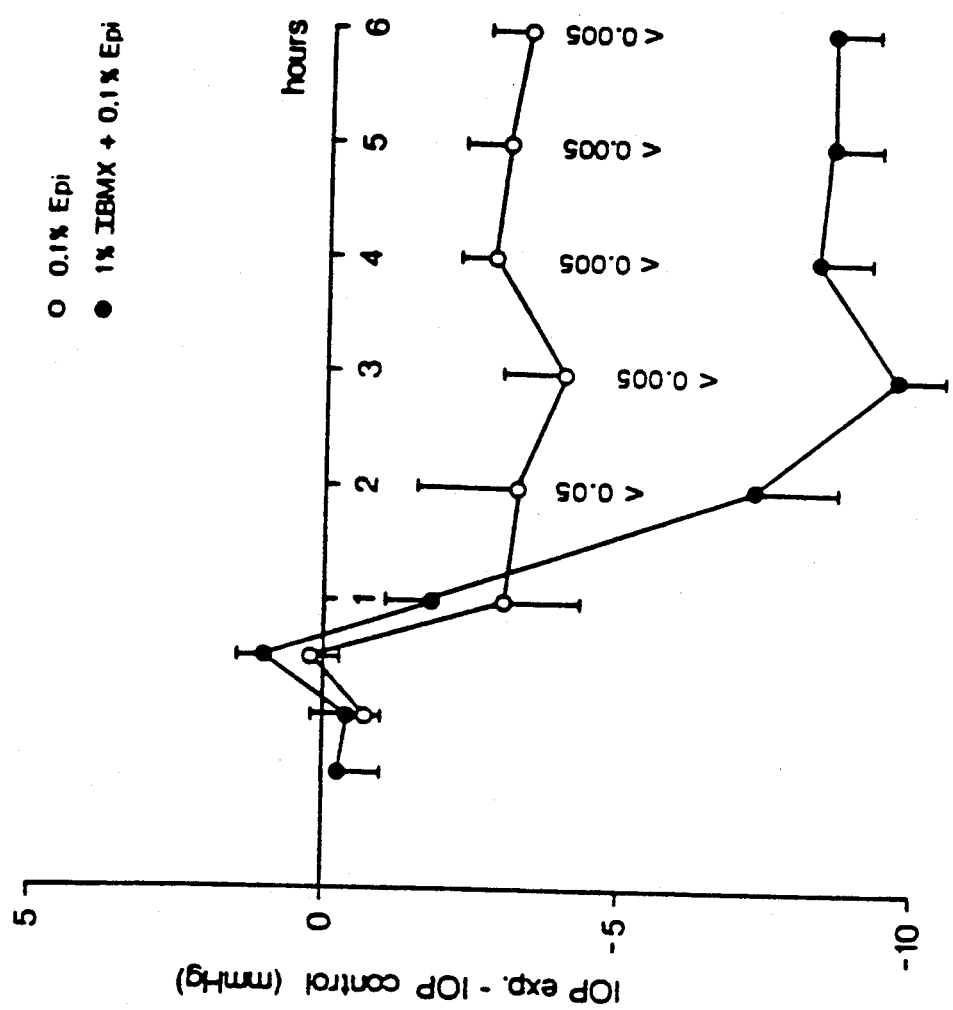
FIG. 9. Difference in intraocular pressure between experimental eyes and control eyes in rabbits treated with 0.1% epinephrine only (empty circles), and in rabbits treated with 1% IBMX and 0.1% epinephrine (dots). Statistical significances indicated as in previous figures.
Figure 10:
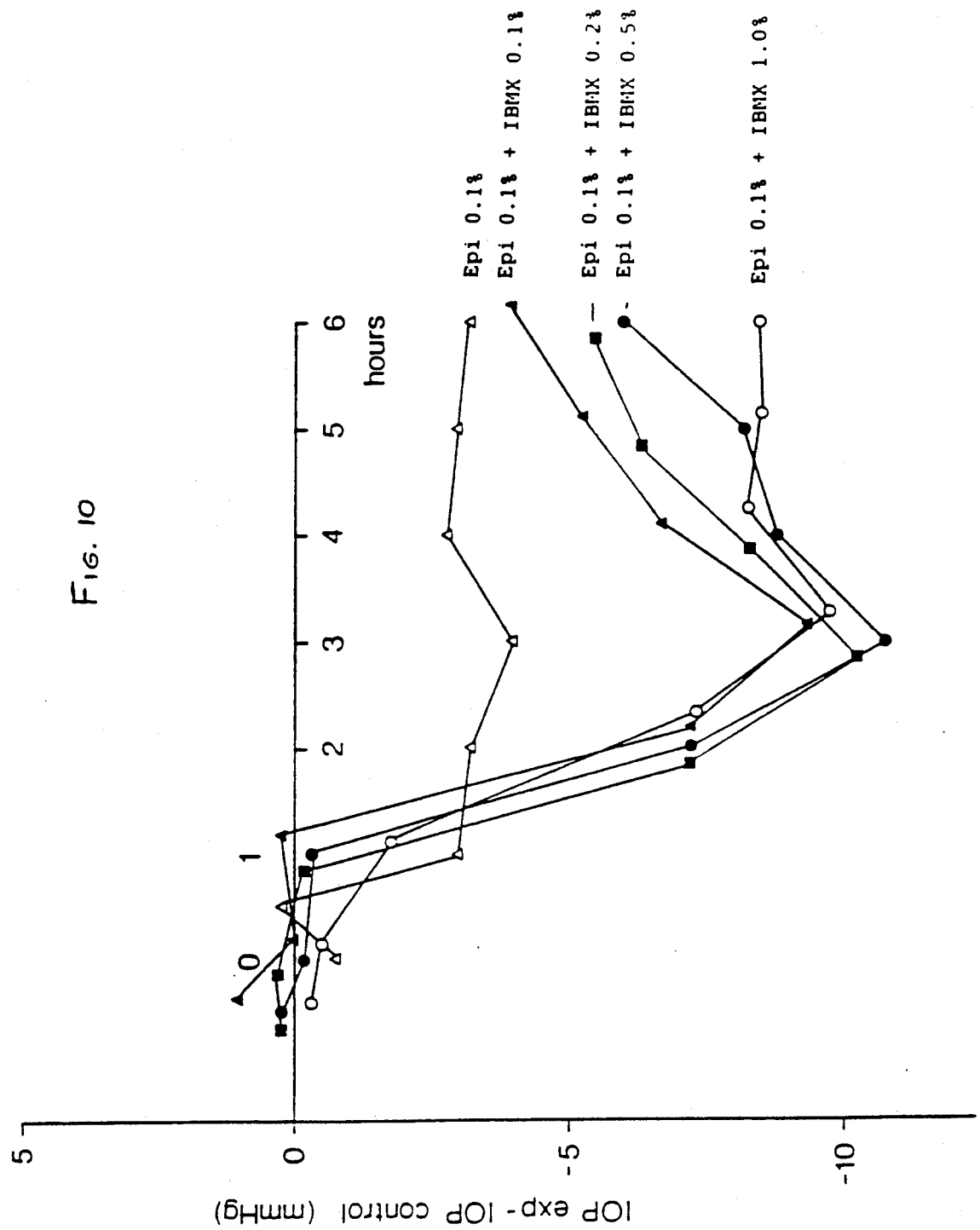
FIG. 10. Difference in intraocular pressure between experimental eyes and control eyes in rabbits treated with 0.1% epinephrine and various concentrations of IBMX.
Figure 11:
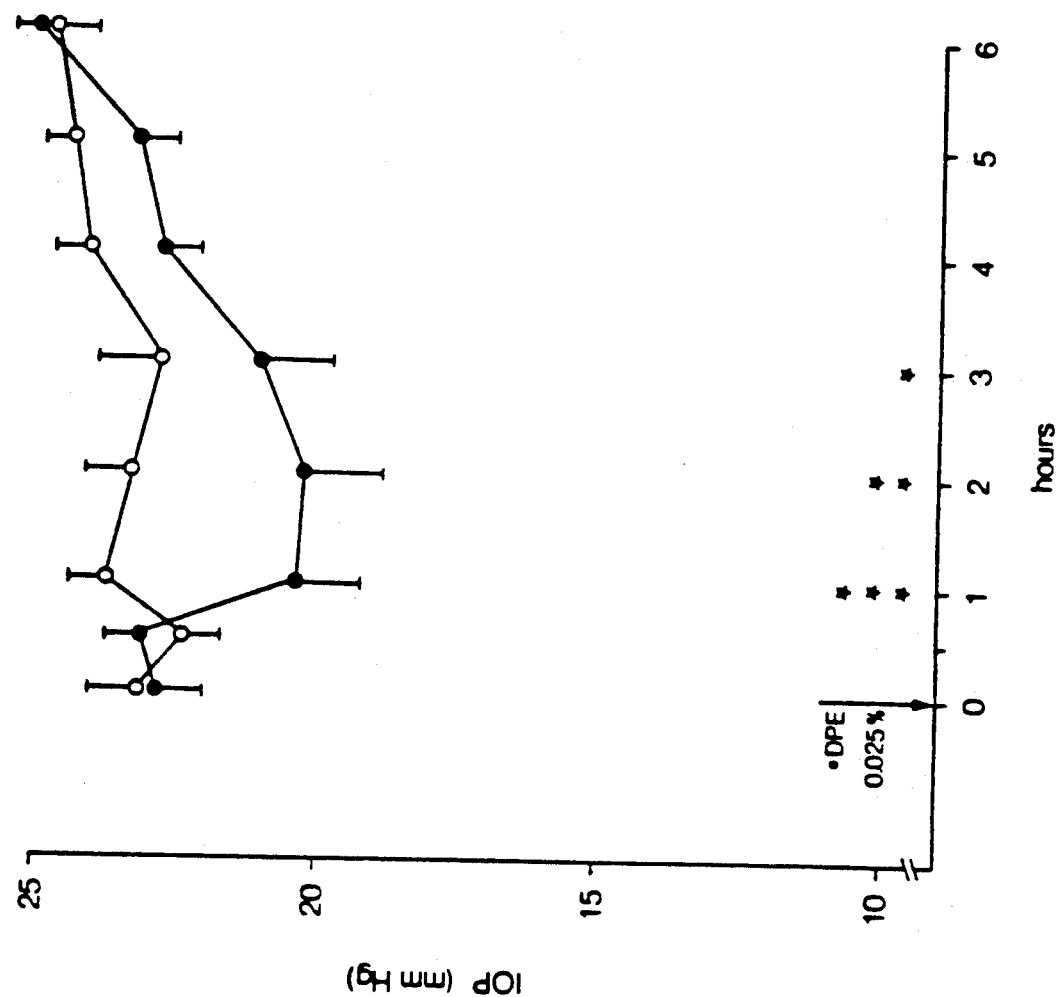
FIG. 11. Effect of 0.025% dipivalylepinephrine on intraocular pressure in rabbits. Empty circles indicate control eyes and dots experimental eyes. Statistical significances between experimental and control eyes indicated by asterisks (*: $p<0.05$, : $p<0.01$, and *: $p<0.001$).
Figure 12:
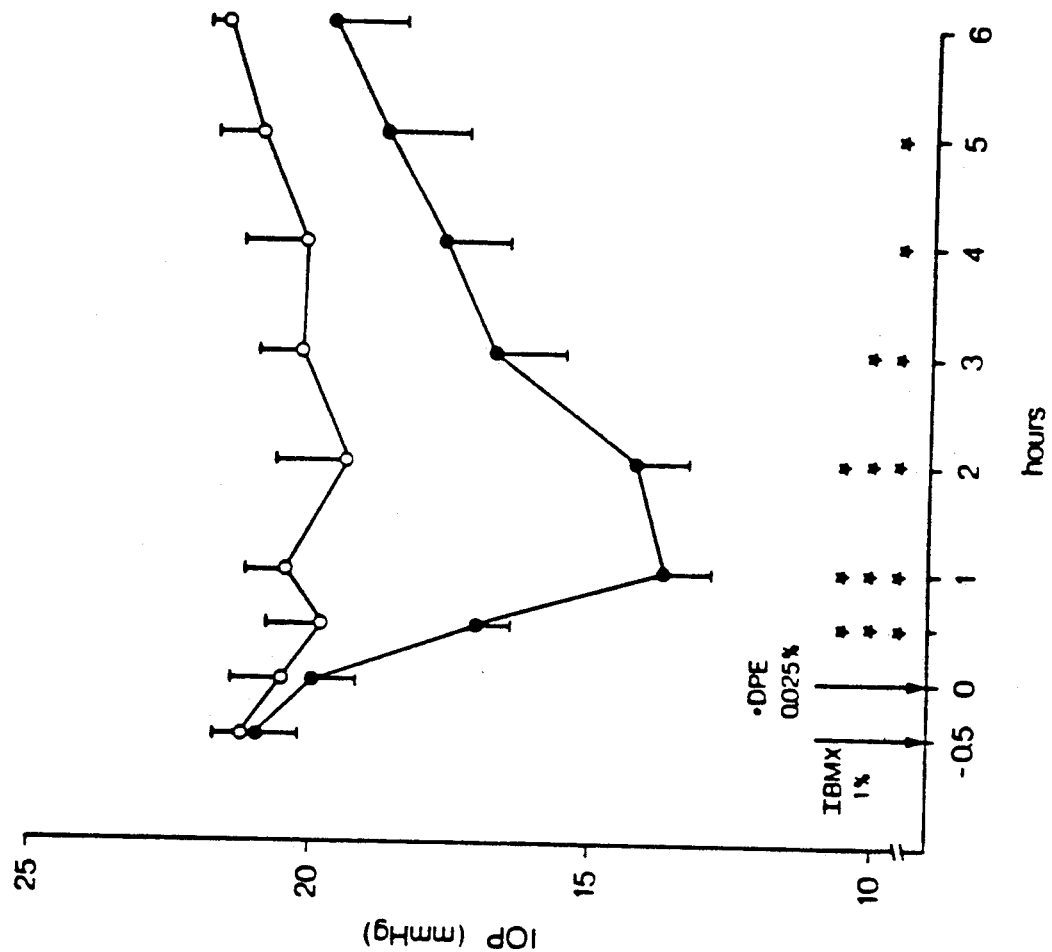
FIG. 12. Effect of 1% IBMX and 0.025% dipivalylepinephrine on intraocular pressure in rabbits. For more details see legend to FIG. 11.
Figure 13:
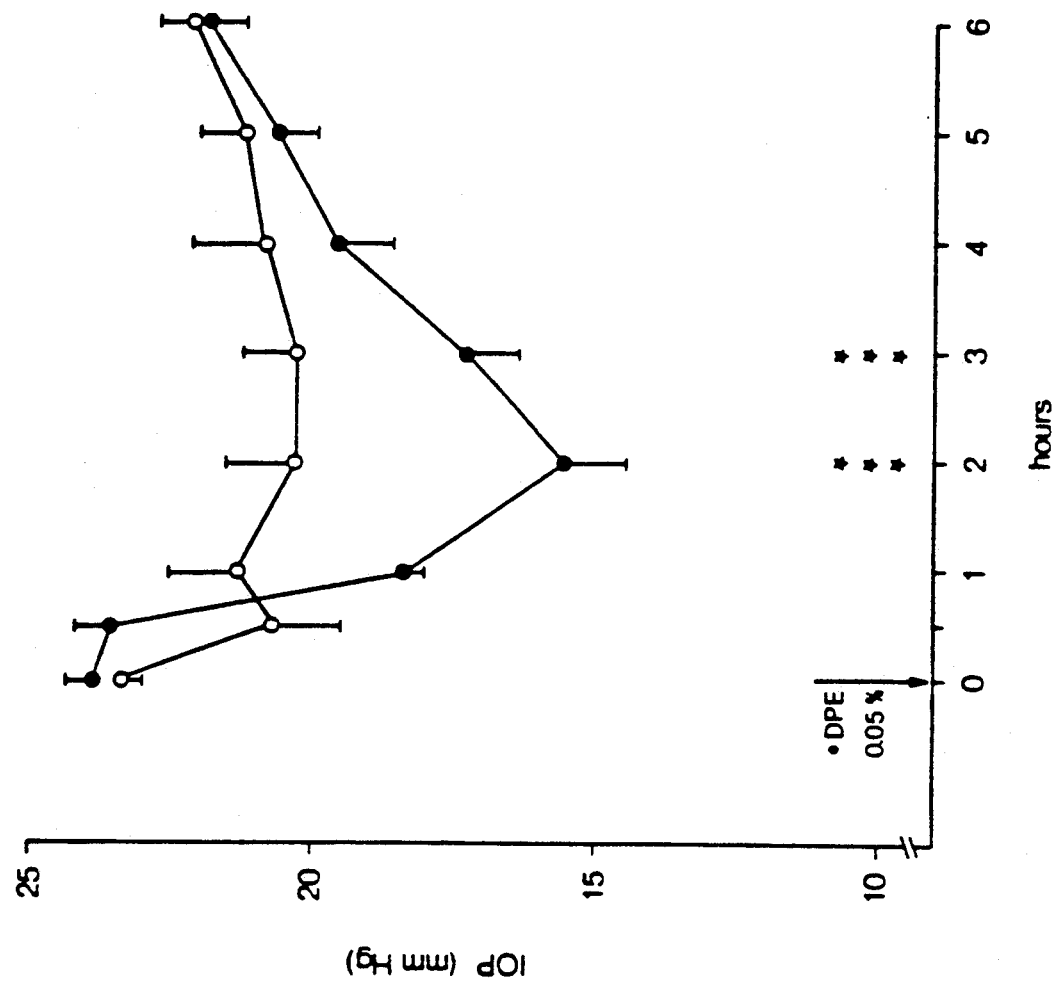
FIG. 13. Effect of 0.05% dipivalylepinephrine on intraocular pressure in rabbits. For more details see legend to FIG. 11.
Figure 14:
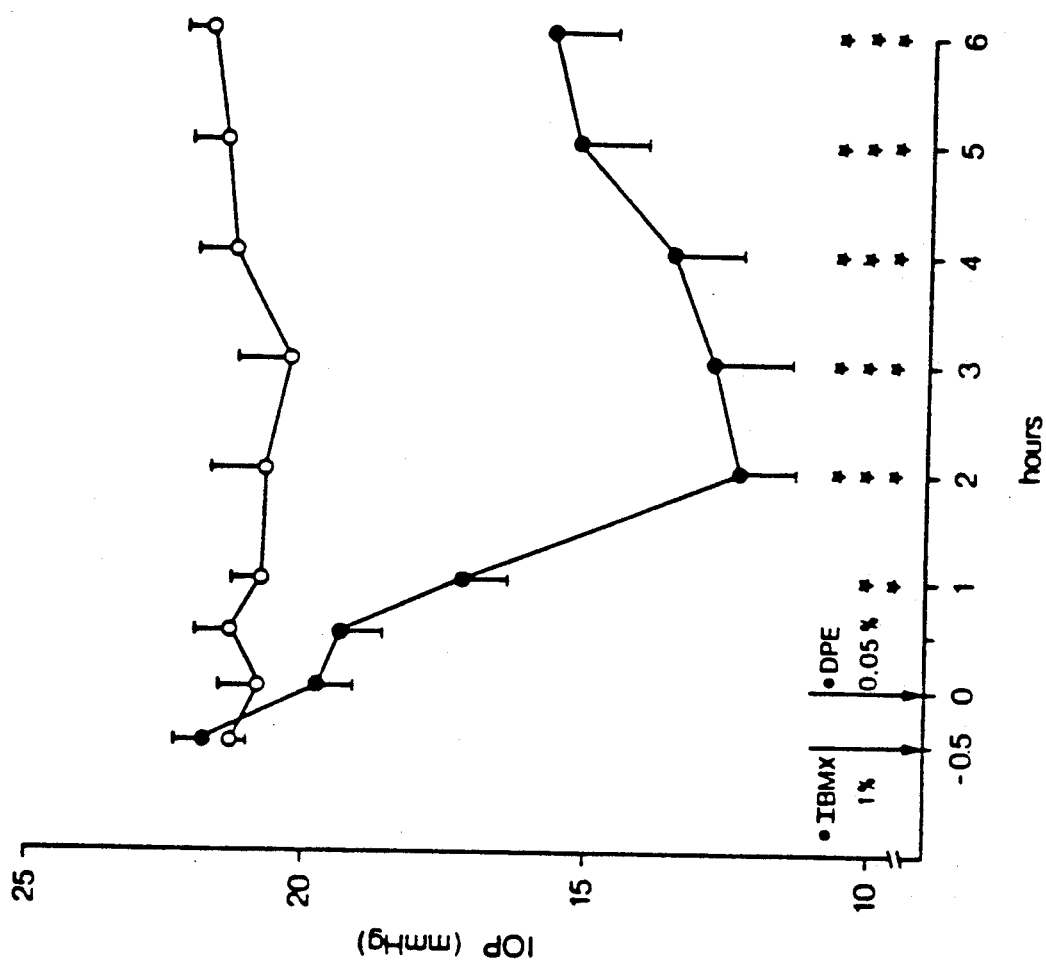
FIG. 14. Effect of 1% IBMX and 0.05% dipivalylepinephrine on intraocular pressure in rabbits. For more details see legend to FIG. 11.
Figure 15:
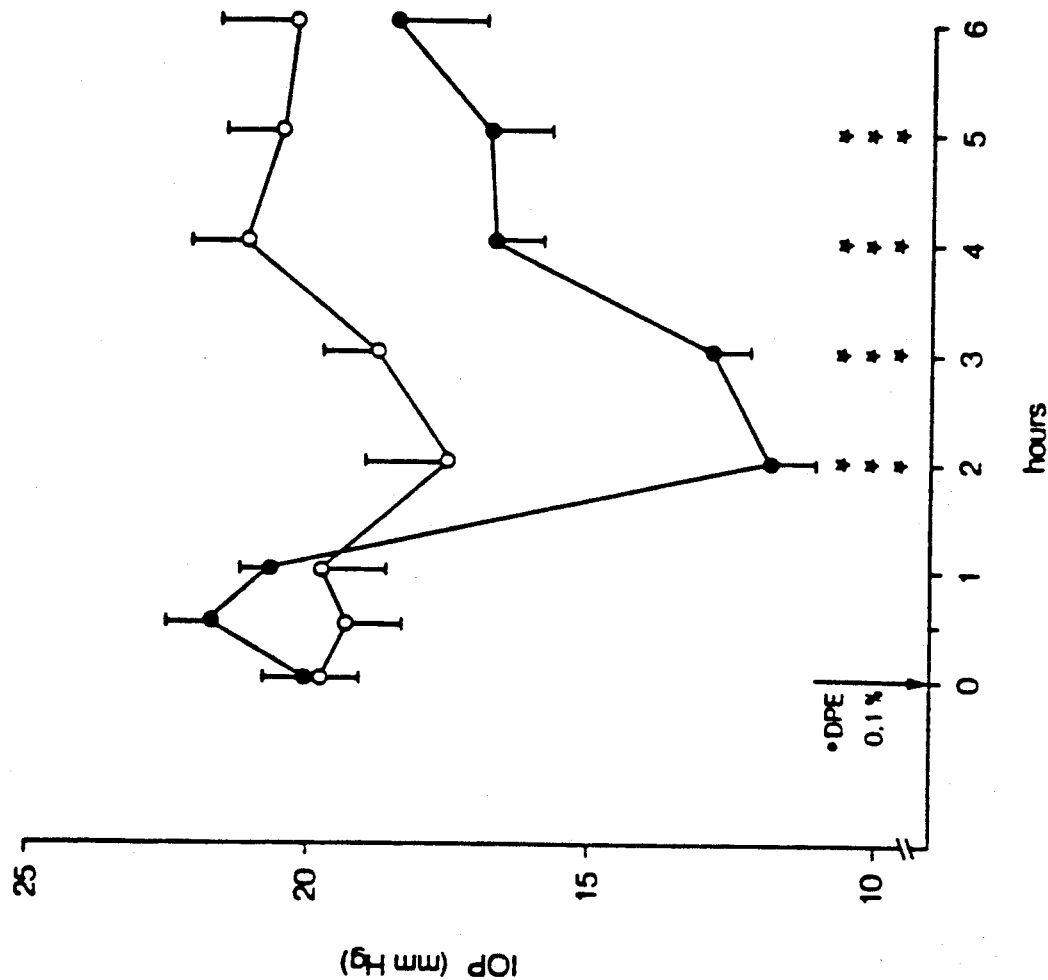
FIG. 15. Effect of 0.1 dipivalylepinephrine on intraocular pressure in rabbits. For more details see legend to FIG. 11.
Figure 16:
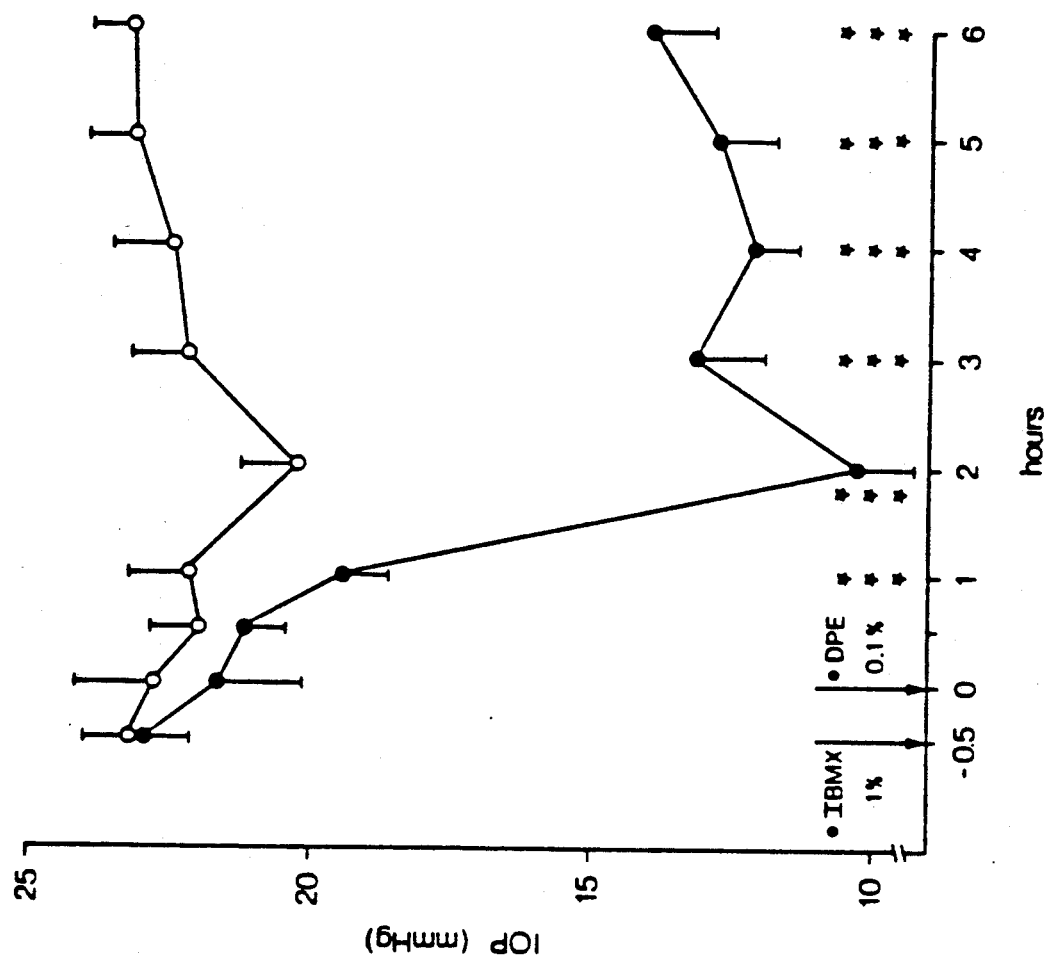
FIG. 16. Effect of 1% IBMX and 0.1% dipivalylepinephrine on intraocular pressure in rabbits. For more details see legend to FIG. 11.
Figure 17:
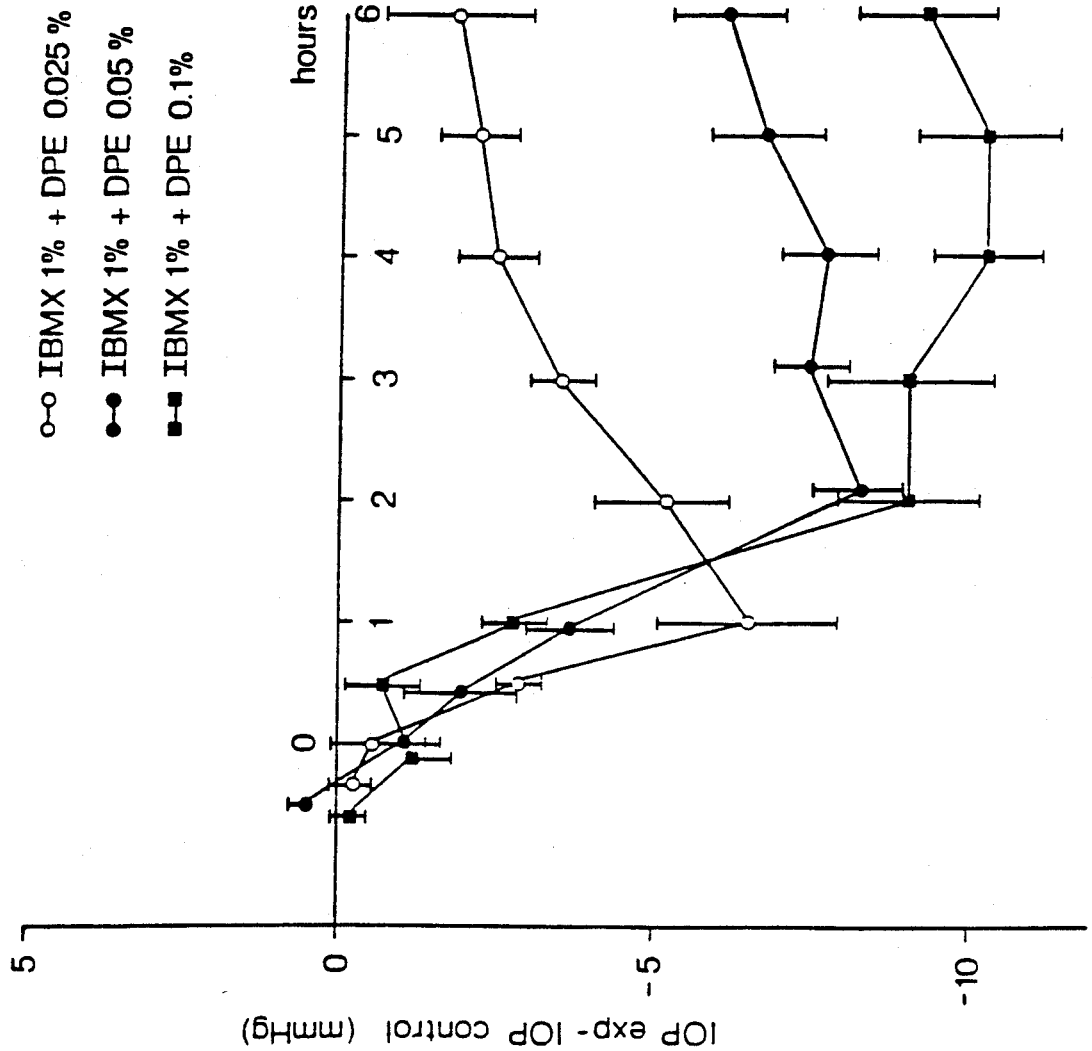
FIG. 17. Difference in intraocular pressure between experimental eyes and control eyes in rabbits treated with 1% IBMX and various concentrations of dipivalylepinephrine.

Furthermore, it is shown (FIGS. 7-9) that in rabbits a combination of (i) 1% isobutylmethylxanthine and (ii) epinephrine in concentrations ranging from 0.025% to 0.1% caused a significant potentation of the intraocular pressure reducing effect as compared to the administration of epinephrine alone in those same concentrations. As demonstrated in FIG. 10 a marked potentation of the intraocular pressure reducing effect of 0.1% epinephrine was obtained with isobutylmethylxanthine in concentrations ranging from 0.1% to 1.0%.

Furthermore, it is shown (FIGS. 11-17) that in rabbits a combination of (i) 1% isobutylmethylxanthine and dipivalylepinephrine in concentrations ranging from 0.025% to 0.1% caused a significant potentation of the intraocular pressure reducing effect as compared to the administration of dipivalylepinephrine alone, in those same concentrations.

Figure 18:
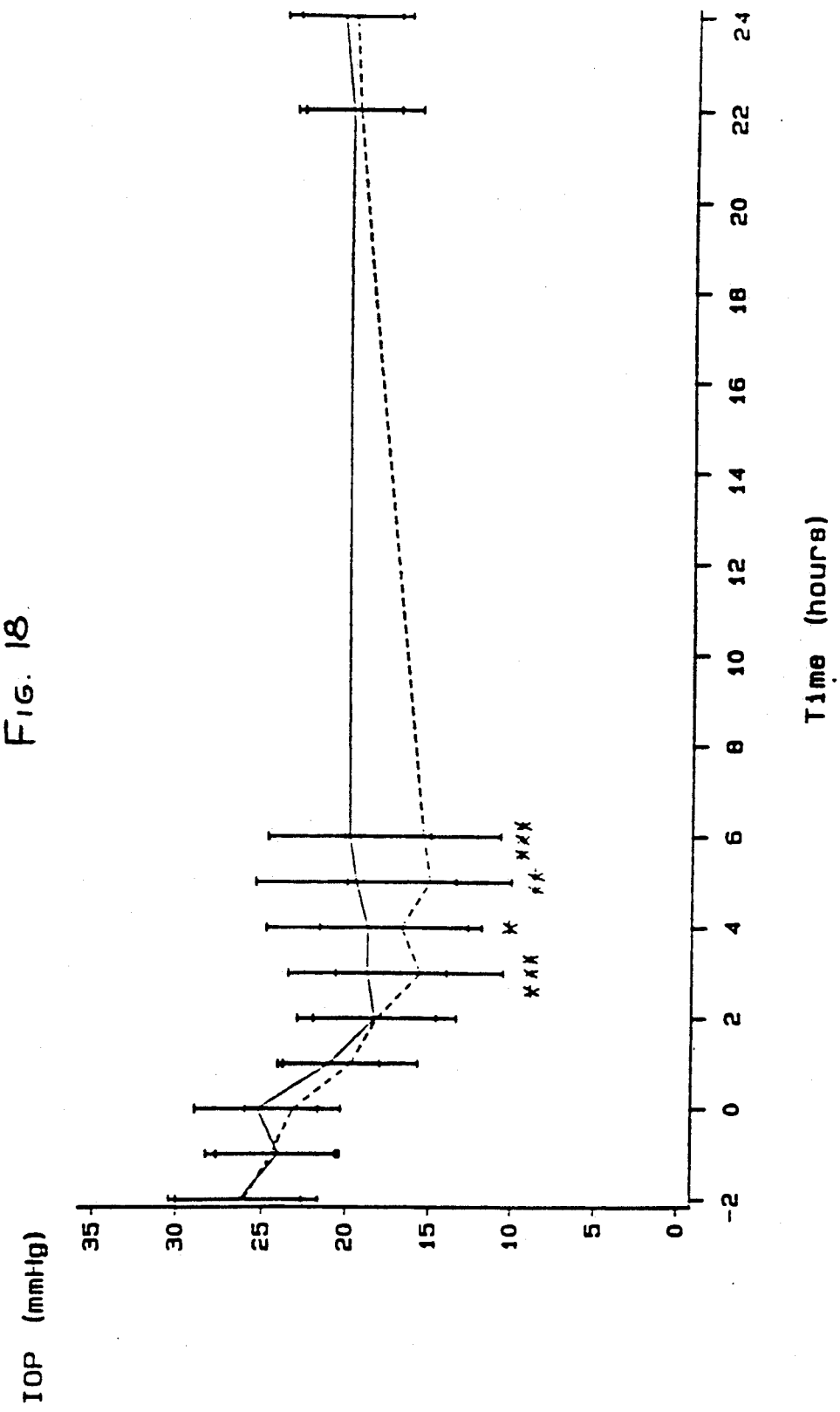
FIG. 18. Intraocular pressure reducing effect of (i) 0.5% epinephrine (solid line) and (ii) 1% IBMX and 0.5% epinephrine (dots) in cats. Statistical significances indicated as in FIG. 11.
Figure 19:
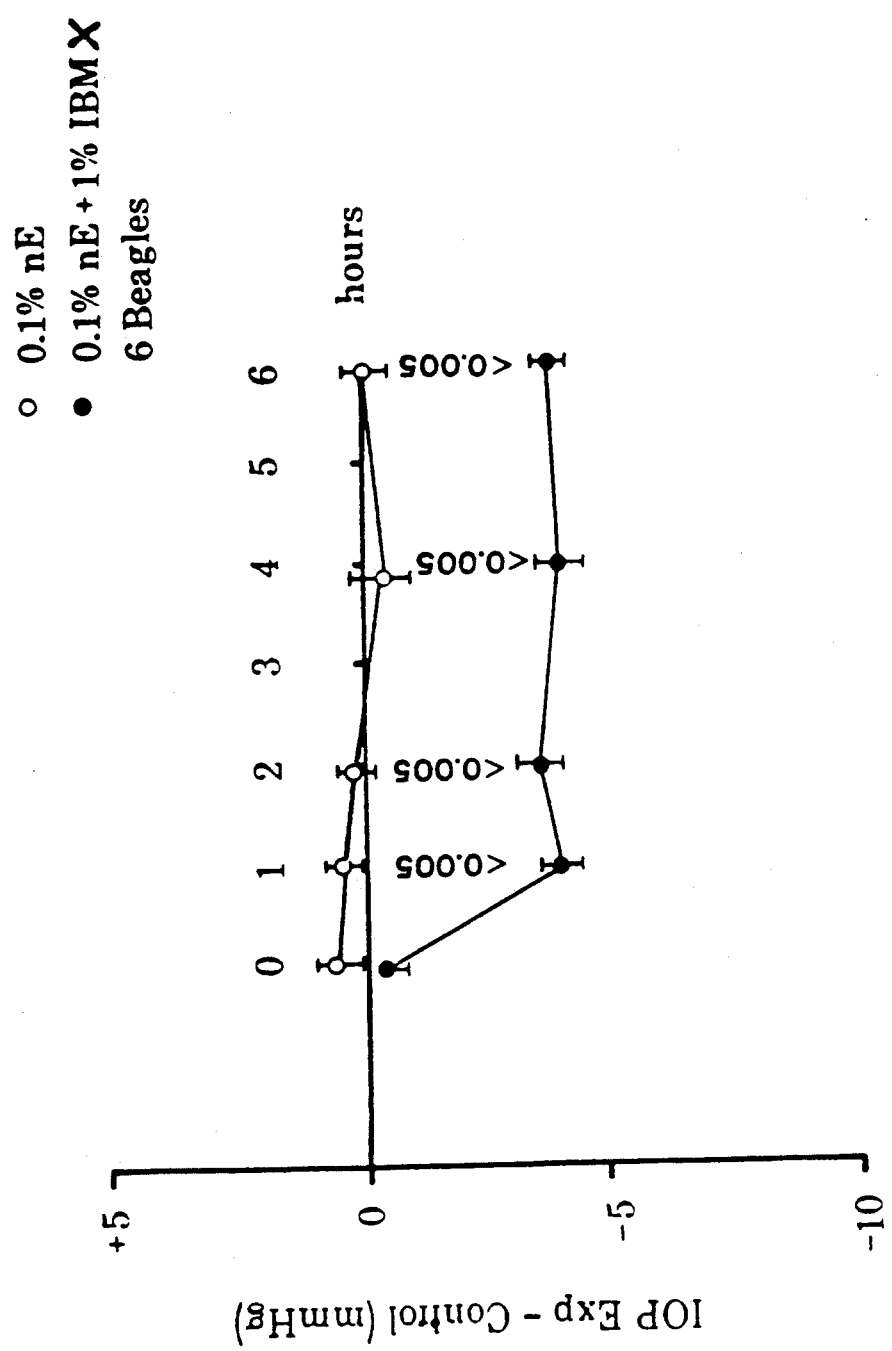
FIG. 19. Difference in intraocular pressure between experimental and control eyes in beagle dogs treated with 0.1% norepinephrine only (empty circles), and in beagle dogs treated with a mixture of 1% IBMX and 0.1% norepinephrine. Statistical significances between the experimental and control eyes indicated between the curves (p-values).
Figure 20:
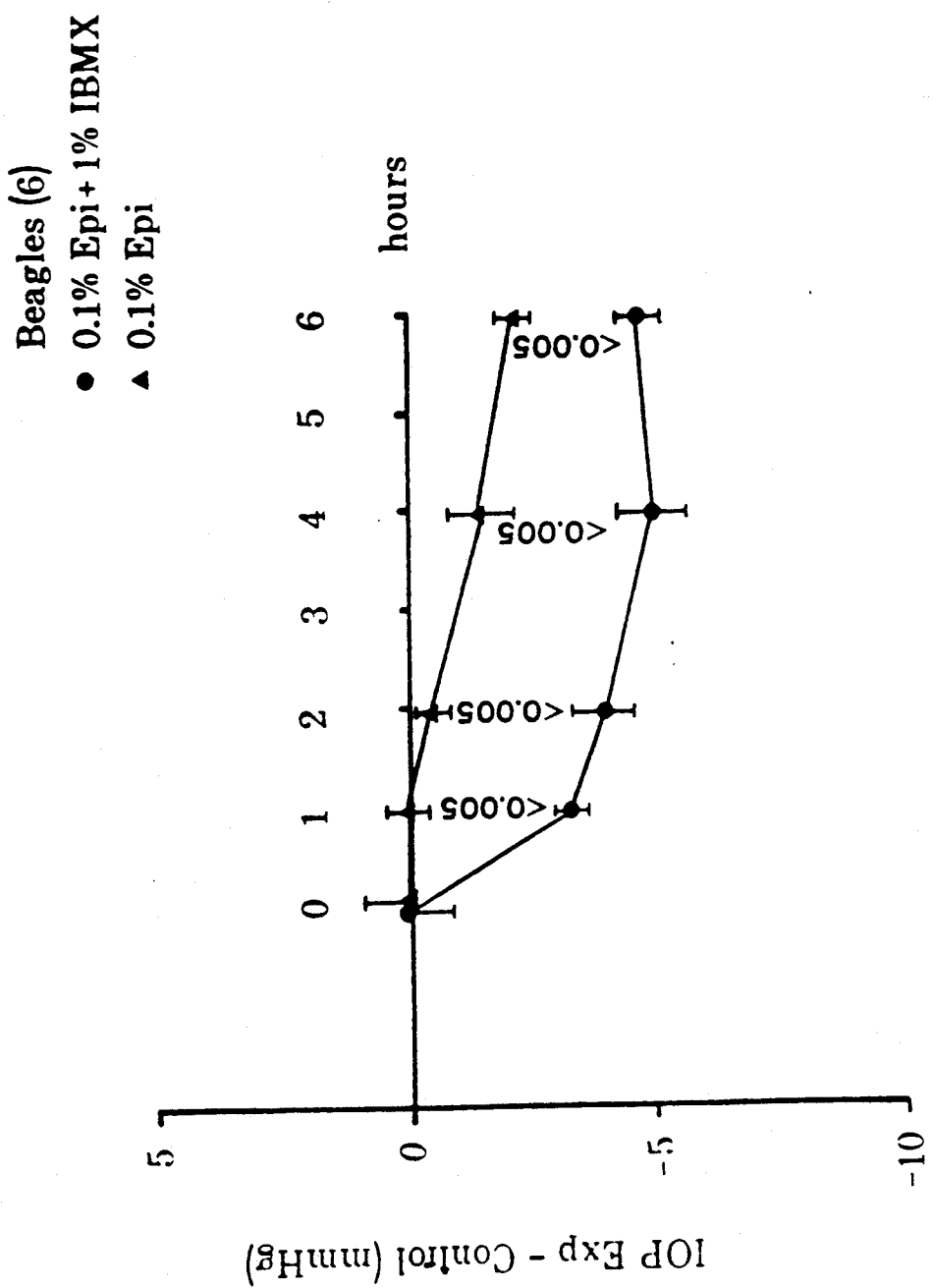
FIG. 20. Difference in intraocular pressure between experimental and control eyes in beagle dogs treated with 0.1% epinephrine only (empty circles), and in beagle dogs treated with a mixture of 0.1% epinephrine and 1% IBMX. Statistical significances indicated as in previous figure.

Furthermore, experiments performed in rabbits, cats and beagle dogs verified that the invention does not only apply to the rabbit species but more generally to mammals, including primates and man, in that a mixture of 1% isobutylmethylxanthine and 0.5% epinephrine in cats significantly potentiated the intraocular pressure reducing effect of 0.5% epinephrine alone in this species (FIG. 18).

The significance of the set of experiments described above is that (1) an unexpectedly strong potentation of the intraocular pressure reducing effect of adrenergic agonists in the presence of isobutylmethylxanthine, i.e. phosphodiesterase inhibition, occurs in rabbits, cats and beagle dogs; (2) this phenomen could be used to advantage in all mammals, including primates and man, for lowering the intraocular pressure in glaucoma and ocular hypertension; (3) this regimen seems to minimize adverse effects in the eye; and (4) the potentation of the response to adrenergic agonists by phosphodiesterase inhibitors enables the use of lesser amounts or adrenergic agonists, thus minimizing systemic and local side effects of these compounds.

We claim:

1. A method for the topical treatment of glaucoma or ocular hypertension which comprises contacting the surface of the eye with a composition consisting essentially of an effective intraocular pressure reducing amount of a mixture of (a) an adrenergic agonist selected from the group consisting of epinephrine, dipivalylepinephrine, norepinephrine, phenylephrine, clonidine, isoproterenol, salbutamol, metaproterenol and terbutaline, and (b) a phosphodiesterase inhibitor selected from the group consisting of isobutylmethylxanthine, theophyllamine, Rolipram and Ro-201724, in an ophthalmically compatible carrier.

2. A method according to claim 1 wherein the phosphodiesterase inhibitor is isobutylmethylxanthine.

3. A method according to claim 2 wherein the adrenergic agonist is epinephrine.

4. A method according to claim 2 wherein the adrenergic agonist is dipivalylepinephrine.

5. A method according to claim 2 wherein the adrenergic agonist is norepinephrine.

6. The method of claim 1 wherein the adrenergic agonist and the phosphodiesterase inhibitor each are present in a concentration of from 1 microgram to 1000 micrograms.

7. The method of claim 1 wherein the adrenergic agonist and the phosphodiesterase inhibitor each are present in a concentration of from 10 micrograms to 100 micrograms.

* * * * *